(12) United States Patent
Beamer (10) Patent No.: US 11,852,509 B2
(45) Date of Patent: *Dec. 26, 2023

(54) CAPACITIVE SENSOR SYSTEMS AND METHOD

(71) Applicant: adidas AG, Herzogenaurach (DE)

(72) Inventor: Bryce Beamer, Herzogenaurach (DE)

(73) Assignee: adidas AG, Herzogenaurach (DE)

( * ) Notice: Subject to any disclaimer, the term of this patent is extended or adjusted under 35 U.S.C. 154(b) by 28 days.

This patent is subject to a terminal disclaimer.

(21) Appl. No.: 17/327,175

(22) Filed: May 21, 2021

(65) Prior Publication Data
US 2021/0275096 A1 Sep. 9, 2021

Related U.S. Application Data

(60) Continuation of application No. 16/692,764, filed on Nov. 22, 2019, now Pat. No. 11,013,463, which is a division of application No. 15/862,138, filed on Jan. 4, 2018, now Pat. No. 10,492,724.

(51) Int. Cl.
| | |
|---|---|
| *G01D 5/24* | (2006.01) |
| *A61B 5/00* | (2006.01) |
| *H05K 1/02* | (2006.01) |
| *H01L 23/538* | (2006.01) |

(52) U.S. Cl.
CPC ............ *G01D 5/24* (2013.01); *A61B 5/6802* (2013.01); *A61B 5/6805* (2013.01); *H01L 23/5387* (2013.01); *H05K 1/0283* (2013.01); *A61B 5/7455* (2013.01); *A61B 2562/0214* (2013.01)

(58) Field of Classification Search
CPC ... A61B 5/6802; A61B 5/6804; A61B 5/6805; A61B 5/6806; G01D 5/24; H01L 23/5387; H05K 1/0283
See application file for complete search history.

(56) References Cited

U.S. PATENT DOCUMENTS

| | | | |
|---|---|---|---|
| 2016/0052131 A1 | 2/2016 | Lessing et al. | |
| 2016/0302699 A1* | 10/2016 | Gal | ............ D04B 21/18 |
| 2017/0176267 A1 | 6/2017 | Keller et al. | |
| 2017/0203184 A1* | 7/2017 | Thompson | ............ A63B 71/06 |
| 2018/0303383 A1* | 10/2018 | Connor | ............ G06F 3/014 |

* cited by examiner

*Primary Examiner* — Suman K Nath
(74) *Attorney, Agent, or Firm* — Sterne, Kessler, Goldstein & Fox P.L.L.C.

(57) ABSTRACT

A capacitive sensor may include a stretchable substrate, a first conductor assembly disposed on the substrate, a second conductor assembly disposed on the substrate and above the first conductor, and a redundancy member coupled to the one of the conductor assemblies. A capacitive sensor may include a first serpentine conductor assembly disposed on the substrate and having first and second terminal ends coupled to the substrate, a second serpentine conductor assembly disposed above and overlapping the first conductor assembly and having first and second terminal ends coupled to the substrate, wherein each of the terminal ends of the first conductor assembly is offset from the corresponding terminal ends of the second conductor assemblies. A sensor system may include a stretchable sensor, an electronics module coupled to the stretchable sensor, and a strain relief member extending from the stretchable sensor and coupling to the electronics module.

12 Claims, 8 Drawing Sheets

CAPACITIVE SENSOR SYSTEMS AND METHOD

CROSS REFERENCE TO RELATED APPLICATIONS

This application is a continuation of U.S. application Ser. No. 16/692,764, filed Nov. 22, 2019, which is a divisional of U.S. application Ser. No. 15/862,138, filed Jan. 4, 2018 (now U.S. Pat. No. 10,492,724), the disclosure of which are incorporated by reference in their entirety.

FIELD OF THE INVENTION

Embodiments of the present invention generally relate to flexible sensor systems, particularly printed capacitive sensor systems used in substrate applications. Additionally included are methods of forming capacitive sensor system, as well as applications of capacitive sensor systems integrated into a garment.

BACKGROUND OF THE INVENTION

Athletic activity is important to maintaining a healthy lifestyle and is a source of entertainment for many people. In more recent years athletes have employed additional tools in an effort to assist in tracking and coaching workouts. For example, GPS and accelerometer based devices may be used to provide speed and distance information when running. Fitness monitoring devices have also been developed that are capable of recording information about an individual's performance during an athletic activity using sensors, and in some cases providing feedback about the individual's performance. Some fitness monitoring devices employ sensors attached to the individual's body, while other fitness monitoring devices rely on sensors attached to a piece of athletic equipment. Such sensors may be capable of measuring various physical and/or physiological parameters associated with the individual's physical activity.

But with respect to providing this information, existing athletic/fitness activity monitoring, training, and coaching systems suffer from a number of drawbacks. Many existing systems are limited in the amount of feedback or coaching that they can give, and may be bulky, heavy, and not integrated into a piece of equipment. For example, many systems require a separate piece of equipment, such as a smart phone, smart watch, other stand-alone wearable device, or the like. These systems are not suitable for monitoring in many real world athletic competitive or training sessions.

Existing garment sensors may measure strain, displacement, and the like but also suffer from several drawbacks. In the case of stretchable garment sensors, e.g., sensors printed using conductive ink, cracks or fissures may develop in one or more of the sensor layers. Cracks may reduce accuracy of the sensor signal, or destroy the signal completely.

BRIEF SUMMARY OF THE INVENTION

What is needed are athletic activity training, and coaching, systems and methods having improved capabilities over existing systems, thus offering individuals engaged in athletic activities and other interested observers better tools to improve their performance through feedback. In this regard, sensors integrated within garments offer an advantage, especially with regard to base layers of clothing worn close to the skin, by providing properly fitting garments that move with the body, allowing sensors to collect accurate and precise data. Also needed are improvements in layering and printing sensors, in particular capacitive sensors. Strain relief systems in printed sensor systems, particularly capacitive sensor systems are also required.

At least some of the embodiments of the present invention satisfy the above needs and provide further related advantages as will be made apparent by the description that follows.

Embodiments of the present invention relate to a capacitive sensor, including a stretchable substrate, a first conductor assembly disposed on the substrate, a second conductor assembly disposed on the substrate and positioned above the first conductor assembly such that the second conductor assembly overlaps the first conductor assembly, and a redundancy member coupled to one of the conductor assemblies.

In some embodiments, a second redundancy member is coupled to the other of the conductor assemblies. In some embodiments, the conductor assemblies have a longitudinal configuration extending in a stretching direction. In some embodiments, the redundancy member has a serpentine configuration including a serpentine peak and a serpentine trough. In some embodiments, the redundancy member is coupled to the first conductor assembly via a junction coupled to the serpentine trough.

In some embodiments, the capacitive sensor further includes a first lead positioned at a terminal end of the first conductor assembly, a second lead positioned at a terminal end of the second conductor assembly and offset from the first lead. In some embodiments, the capacitive sensor further includes a first lead positioned at a terminal end of the first conductor assembly, a second lead positioned at a terminal end of the second conductor assembly and extending substantially parallel to the first lead. In some embodiments, a first lead is positioned at a terminal end of the first conductor assembly and extending substantially perpendicular to a longitudinal axis of the first conductor assembly, a second lead positioned at a terminal end of the second conductor assembly and extending substantially parallel to the first lead.

In some embodiments, the redundancy member is configured to absorb stress in the stretching direction. In some embodiments, the first conductor assembly includes a silver ink layer, a carbon ink layer disposed above the silver ink layer, and an insulation layer disposed above the carbon ink layer.

Embodiments of the present invention also relate to a capacitive sensor including a stretchable substrate, a first serpentine conductor assembly disposed on the substrate and having first and second terminal ends coupled to the substrate, and a second serpentine conductor assembly disposed above and overlapping the first conductor assembly and having first and second terminal ends coupled to the substrate, wherein a terminal end of the first conductor assembly is offset from the corresponding terminal end of the second conductor assemblies. In some embodiments the first serpentine conductor assembly includes a silver ink layer, a carbon ink layer disposed above the silver ink layer, and an insulation layer disposed above the carbon ink layer. In some embodiments, the second serpentine conductor assembly includes a silver ink layer, a carbon ink layer disposed above the silver ink layer, and an insulation layer disposed above the carbon ink layer. In some embodiments, the first terminal end of each of the conductor assemblies extend substantially parallel to one another. In some embodiments, the first terminal end of each of the conductor assemblies is offset from one another.

Embodiments of the present invention also relate to a sensor system, including a stretchable sensor responsive to stretching along a stretching axis, an electronics module in a housing coupled to the stretchable sensor, a strain relief member extending from the stretchable sensor and coupling to the electronics module. In some embodiments, the strain relief member extends off axis to the stretching direction. In some embodiments, the strain relief member is configured such that the sensor does not respond to movement of the strain relief member. In some embodiments, the housing is encapsulated in a garment. In some embodiments, the stretchable sensor and the housing are encapsulated in a garment.

Additional features of embodiments of the invention will be set forth in the description that follows, and in part will be apparent from the description, or may be learned by practice of the invention. Both the foregoing general description and the following detailed description are exemplary and explanatory and are intended to provide further explanation of the invention as claimed.

BRIEF DESCRIPTION OF THE DRAWINGS/FIGURES

The accompanying figures, which are incorporated herein, form part of the specification and illustrate embodiments of the present invention. Together with the description, the figures further serve to explain the principles of and to enable a person skilled in the relevant arts to make and use the invention.

DETAILED DESCRIPTION OF THE INVENTION

The present invention will now be described in detail with reference to embodiments thereof as illustrated in the accompanying drawings. References to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, non-transitory tangible computer readable or computer usable storage media having instructions stored thereon, or a combination thereof, and may be implemented in one or more computer systems or other processing systems.

The methods and systems discussed above are further described below. The figures below may apply to both the method and system embodiments of the invention. While capacitive sensor systems are described, the various methods and systems described herein may be applied to other types of sensor systems, for example, resistive, inductive, etc.

Strain sensors in general are used to measure strain on an object. In some instances, a common type of strain gauge consists of an insulating flexible backing which supports a metallic foil pattern. The gauge is attached to the object by a suitable adhesive. As the object is deformed, the foil is also deformed, causing its electrical resistance to change. This resistance change, usually measured using a Wheatstone bridge, is related to the strain by the quantity known as the gauge factor.

Capacitance is the ability of a system to store an electric charge, that is, the ratio of the charge in a system to the corresponding change in its electric potential. Further, in the case of a parallel plate capacitor, capacitance is directly proportional to the surface area of the conductor plates and inversely proportional to the separation distance between the plates. That is, if the area of the conductor plates are increased, a capacitance measurement increases. Similarly, if the separation distance between the plates is decreased, a capacitance measurement increases. Other configurations of capacitive sensors rely on capacitance changing based on particular geometrical relations between components changing. Thus, certain dimensional relationships between components may be applied as above to correlate change in capacitance with a change in strain. This is in contrast to resistive-strain sensor applications. Compared to capacitive applications, resistance based sensors generally suffer from high levels of hysteresis and high levels of signal noise.

Figure 1A:
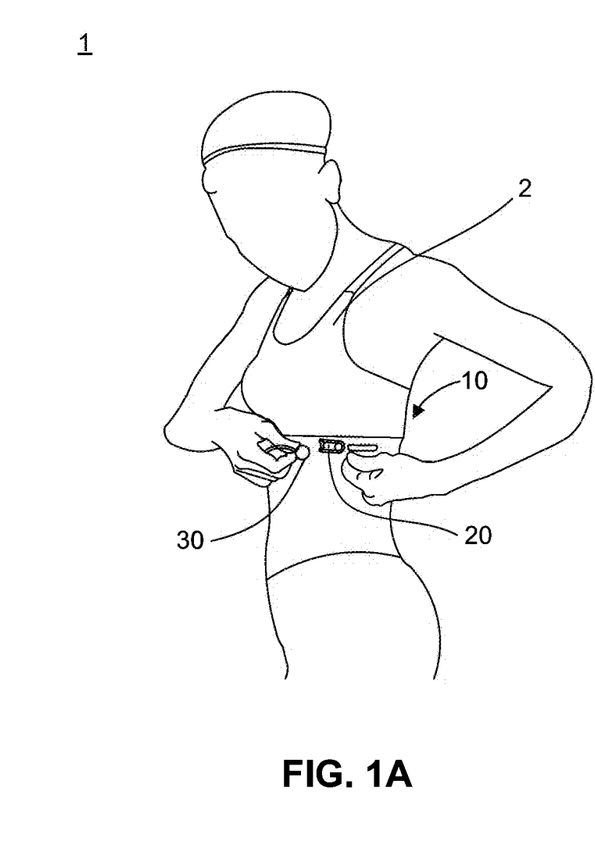
FIGS. 1A and 1B are illustrations of an individual using a sensor system integrated into a garment according to an embodiment of the present invention.
Figure 1B:
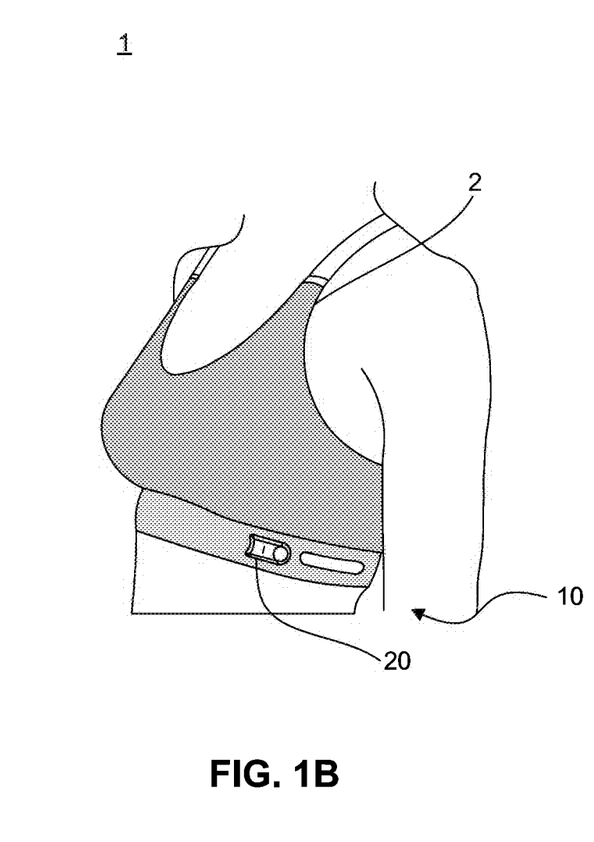

Turning to FIGS. 1A and 1B, individual 1 is shown using a garment 2, particularly a sports bra, with capacitive sensor system 10 operatively coupled to electronic module 20. As shown in FIG. 1A, the system 10 or electronic module 20 may be coupled to data or charging system 30, for example, to download sensor data or charge the electronic module. In use, however, data or charging system 30 may be wireless such that individual 1 is free to move without the need for extra components, such as wires or cable connections. Embodiments of the present invention may incorporate features of motion and performance monitoring systems. Exemplary motion monitoring and performance systems are disclosed in commonly owned U.S. patent application Ser. No. 13/077,494, filed Mar. 31, 2011 (which published as U.S. Patent App. Pub. No. 2012/0254934), and commonly owned U.S. patent application Ser. No. 13/797,361, filed Mar. 12, 2013 (which published as U.S. Patent App. Pub. No. 2014/0266160), the entirety of each being incorporated herein by reference thereto.

Figure 2:
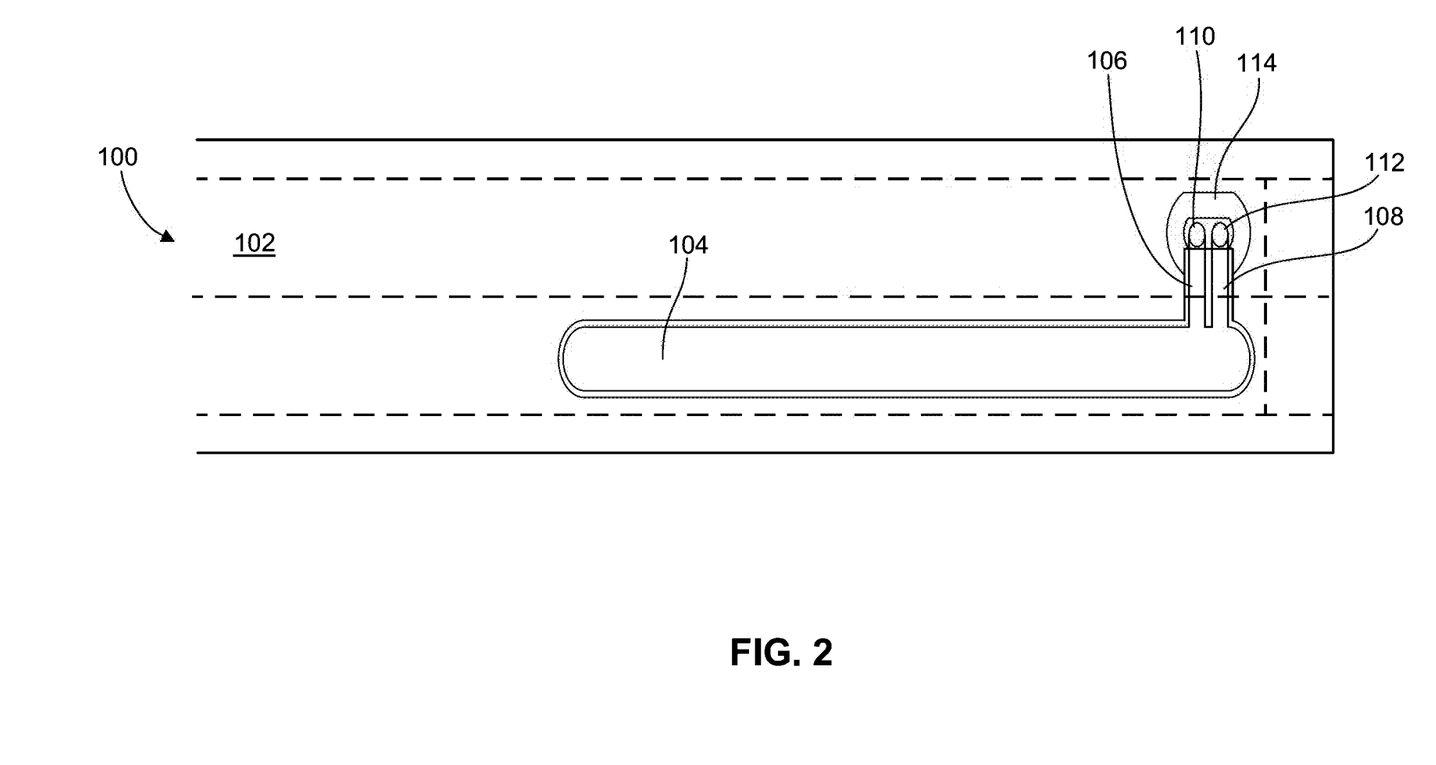
FIG. 2 is an illustration of a capacitive sensor system according to embodiments of the present invention.

As shown in FIG. 2, some embodiments are directed to capacitive sensor systems 100, including a substrate, e.g., stretchable substrate 102. As shown, substrate 102 may be operatively coupled with capacitive area 104, formed for example with conductive ink. As described below, with reference to FIG. 5, capacitive sensor systems disclosed may include at least two conductor assemblies, for example, conductor assembly 500 and conductor assembly 600, disposed below conductor assembly 500, which define capacitive area 104. Further detail of the construction and layering of the conductor assemblies into a finished capacitive sensor system, including substrate structure is provided below, with reference to FIG. 5.

Capacitive area 104 may extend along a stretching direction of substrate 102, such that when an individual moves along the stretching direction, the area of capacitive area 104 changes, which results in a change in capacitance. As shown, in some embodiments, capacitive sensor system 100 includes leads 106/108 that are screen printed in the same way as capacitive area 104, and extend substantially perpendicular to capacitive area 104. Leads 106/108 may include terminal ends 110/112, that connect to connection pad 114, such that the electrical signal (e.g., change in capacitance that may be converted to a strain measurement) from the sensor may be transmitted through the system to, for example, an electronic module (not shown).

As above, capacitance in a parallel plate capacitor is calculated as the area of the capacitive plates divided by the distance between them, multiplied by a permittivity constant. In this regard, a measured capacitance change due to stretching the sensor and thus changing the capacitive area 104, for known permittivity and constant or estimated distance between layers of conductor assemblies 500/600, strain may be sensed or calculated based on the change in the capacitive area 104.

As shown in FIG. 2, during repeated use, the printed sensor layers in capacitive area 104 may develop cracks or fissures, due to repeated strain cycling, prolonged strain, or large stress magnitudes. Various factors contribute to the formation of cracks or fissures, including direction of strain, material or manufacturing variation, number of cycles, length of strain, types of or magnitudes of stress, etc. This decreases the effective capacitive area 104 as the circuit becomes incomplete, and may reduce accuracy of the sensor or destroy the sensor completely, as it cuts off a large amount of capacitive area 104 from the ultimate sensor circuit.

Figure 3:
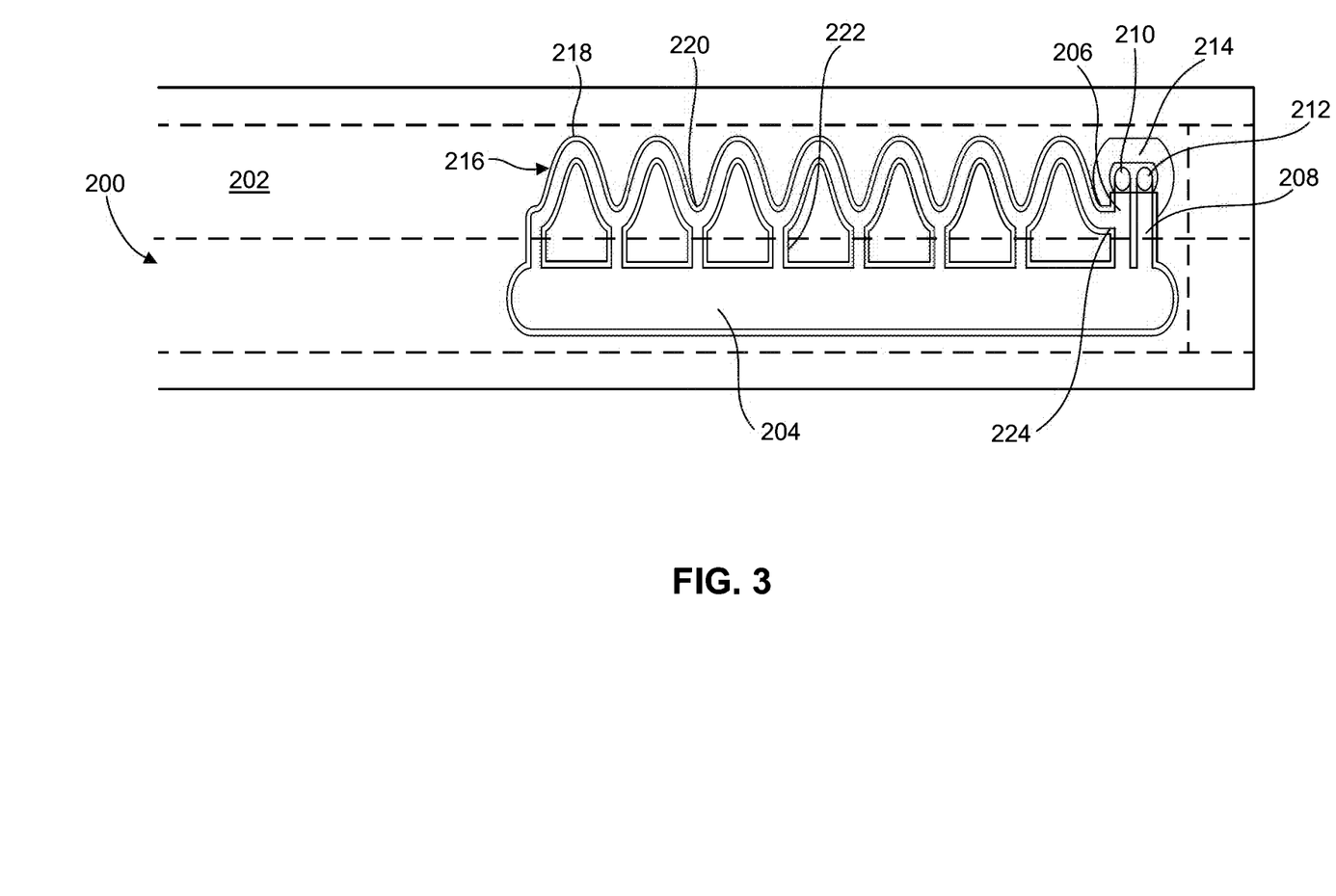
FIG. 3 an illustration of a capacitive sensor system according to embodiments of the present invention.

As shown in FIG. 3, in some embodiments, capacitive sensor 200 includes many of the same components as capacitive sensor system 100, such as substrate 202, capacitive area 204, leads 206/208 that extend substantially perpendicular to capacitive area 204. Leads 206/208 may include terminal ends 210/212 that connect to connection pad 214. Additionally, in some embodiments, capacitive sensor 200 includes redundancy member 216. Redundancy member 216 may include generally serpentine peaks 218 and troughs 220, and may be printed in the same manner as capacitive area 204. Redundancy member 216 and capacitive area 204 are operatively and structurally coupled at junctions 222. In some embodiments, redundancy member 216 may be operatively and structurally coupled to one or more of the conductor assemblies 500/600, at junctions 222. Redundancy member 216 may include lead 224 that connects to lead 206 or 208, for example. In some embodiments, redundancy member 216 connects directly to connection pad 214.

In some embodiments the first and second leads 206/208 may extend substantially parallel to one another. In some embodiments, first and second leads 206/208 may extend such that they do not overlap one another, in contrast to the capacitive area 204, where conductor assemblies 500/600 may overlap one another.

In some embodiments, redundancy member 216 is configured to absorb stress in the stretching direction. As shown, even if capacitive sensor 200 develops cracks or fissures through capacitive area 204 through repetitive strain cycling, the connection to the overall circuit is not completely disrupted because the capacitive area is still coupled via redundancy member 216 at junctions 222. Advantageously, the generally serpentine structure including peaks 218 and troughs 220 lend greater flexibility to the printed layers, and resist the development of cracks and fissures over repeated strain cycling. In some embodiments, the curved nature of the generally serpentine structure induces bending/buckling out of plane relative to the general plane of the sensor, which increases strain relief and avoids formation of fissures or cracks due to material fatigue from either strain cycling or large stress magnitudes. In some embodiments the conductor assemblies 500/600 have a longitudinal configuration extending in a stretching direction. In some embodiments, redundancy member 216 has a serpentine configuration, including at least a serpentine peak and a serpentine trough. In some embodiments, redundancy member 216 is coupled to the one of the conductor assemblies 500/600 via junction 222 coupled to the serpentine trough.

As used herein, "serpentine" includes waveform patterns of constant or variable amplitudes, generally sinusoidal patterns, curvilinear forms, "horseshoe" type waveforms where the peaks and troughs are nested next to one another, etc.

Figure 4:
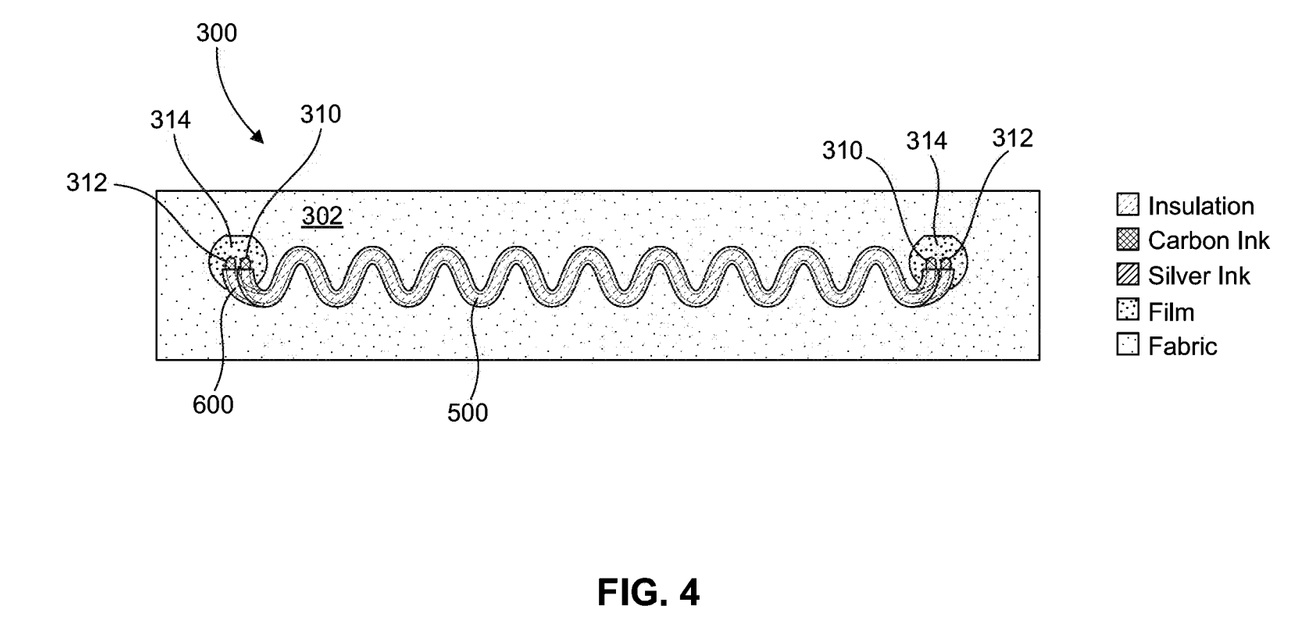
FIG. 4 is an illustration of a capacitive sensor system according to embodiments of the present invention.
Figure 5:
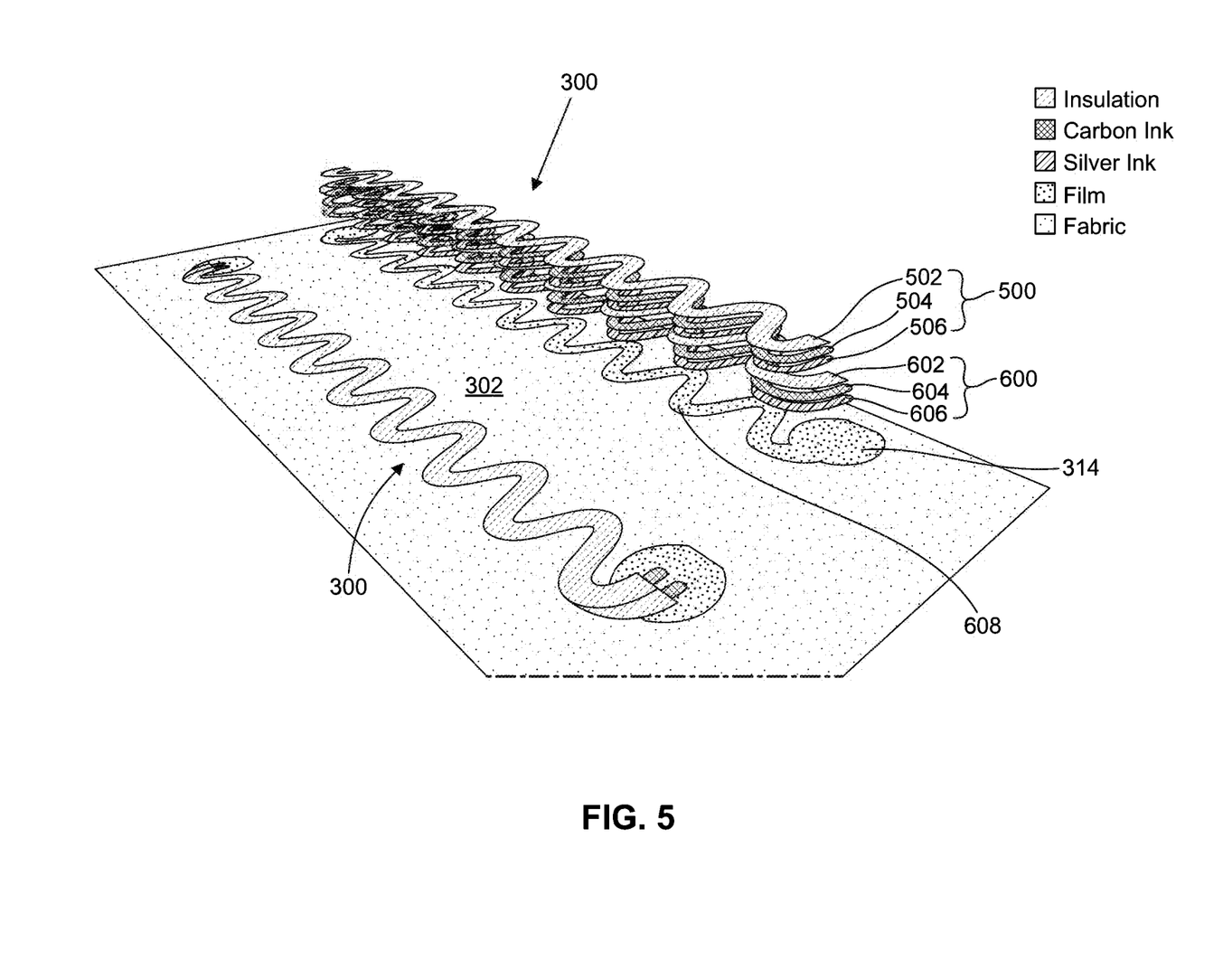
FIG. 5 is a partial exploded view of the capacitive sensor system shown in FIG. 4 according to embodiments of the present invention.

As shown in FIGS. 4 and 5, in some embodiments, first conductor assembly 600 is disposed on the substrate, and second conductor assembly 500 is disposed on the substrate and above the first conductor assembly such that the second conductor assembly generally overlaps the first conductor assembly. In some embodiments, a first lead 312 is positioned at a terminal end of the first conductor assembly 600, and a second lead 310 is positioned at a terminal end of the second conductor assembly 500 and offset from the first lead 312. In some embodiments, leads 310/312 extend substantially parallel to the one another. In some embodiments, one or more of leads 310/312 extend substantially perpendicular to one or more of the conductor assemblies. In some embodiments, the first terminal end of each of the conductor assemblies extend substantially parallel to one another. In some embodiments, the first terminal end of each of the conductor assemblies is offset from one another. In some embodiments, the second terminal end of each of the conductor assemblies extend substantially parallel to one another. In some embodiments, the second terminal end of each of the conductor assemblies is offset from one another. In some embodiments, the conductor assemblies 600/500 are used as a conductor for other sensors or actuators beyond capacitive sensors. Each of the conductive assemblies or layers as described herein may be similarly used for conducting components for other sensors or actuators beyond capacitive sensors.

As shown in FIGS. 4 and 5, in some embodiments, the capacitive area may be configured as a serpentine structure including peaks 318 and troughs 320, taking advantage of additional flexibility in configuration. As shown, in some embodiments, a first serpentine conductor assembly 600 may be disposed on the substrate and having first and second terminal ends 312 coupled to the substrate 302, a second serpentine conductor assembly 500 disposed above and overlapping the first conductor assembly 600 and having first and second terminal ends 310 coupled to the substrate, wherein a terminal end of the first conductor assembly 600 is offset from the corresponding terminal end of the second conductor assembly 500. In some embodiments, the serpentine structure may have a predetermined frequency, dimensions, pitch, etc. In some embodiments, these dimensions may vary along the length of sensor 300, or may be constant.

To illustrate the general layering structure of capacitive sensor systems 100, 200, and 300, FIG. 5 shows a partial exploded view of an exemplary layering structure according to an embodiment of various capacitive sensor systems as disclosed herein. As shown, capacitive sensor systems 100, 200, and 300 may include at least two conductor assemblies, for example, conductor assembly 500 and conductor assembly 600, disposed below conductor assembly 500. As shown, each conductor assembly may be configured with multiple layers, for example, a layer of conductive ink 606/506, such as silver ink, may be followed with an intermediate layer of conductive ink 604/504, such as carbon ink. In some embodiments, an insulation layer 602/502 may be disposed above intermediate layer 604/504. In some embodiments, the number of conductive layers, type of material, order of materials, etc., may be varied. With reference to embodiments including redundancy member 216, in some embodiments, redundancy member 216 may be formed only in some of the particular layers of conductor assemblies 500/600. In some embodiments, redundancy member 216 may include different geometries at different layers of conductor assemblies 500/600.

In some embodiments, the base layer of the conductive assembly smooths the printing surface for subsequent layers. In general, carbon layers tend to me more stable, durable, and washable, but have lower conductivity. In contrast, silver layers are less durable but offer relatively higher conductivity at the expense of increased cost. In some embodiments, layers including carbon are used to protect layers including silver, and may also lower cost. Additionally, other types of layers, such as silver-silver chloride may improve certain types of additional physiological signals, such as EMG or ECG signals. In some embodiments, insulation layers are printed to reduce the number of films needed, or to extend the performance of the films, or improve the performance of the capacitive sensor. In some embodiments, insulation is positioned between adjacent conductive layers. In some embodiments, insulation is positioned between capacitive assemblies and other capacitive or conductive bodies, (e.g., the body of a subject, a sweaty fabric).

In some embodiments, multiple layers of conductors or conductive assemblies reduce signal noise generated from the body. In some embodiments, multiple layers of conductors or conductive assemblies may be used as an input sensor, such as a touch sensor.

As shown, in some embodiments, the layers of each of the conductor assemblies may be separately printed, for example, screen printed or ink jet printed, as traces disposed on top of each other in layers, prior to integration with the garment. In some embodiments, the layers are printed (e.g., screen printed, ink-jet printed, direct deposition, stenciling, etc.) and then cut (e.g., laser cut, die cut, etc.) out to their desired shape prior to integration. In some embodiments, a film layer 608 may be used as a bottom-most layer on one or more of the conductor assemblies 500/600, acting as an effective platform for one or more of the conductor assemblies. In some embodiments, film layer 608 may be, for example a polyurethane film. In this regard, film layer 608 is configured as a stretchable layer. In some embodiments, film layer 608 may be predisposed on substrate 302. In some embodiments, film layer 608 may be applied to substrate 302 once the conductor assemblies have been printed onto it. In some embodiments, the conductor assemblies 500/600 may be stacked, and then applied to substrate 302, such as a fabric for a garment, for example, through heat pressing.

Figure 6:
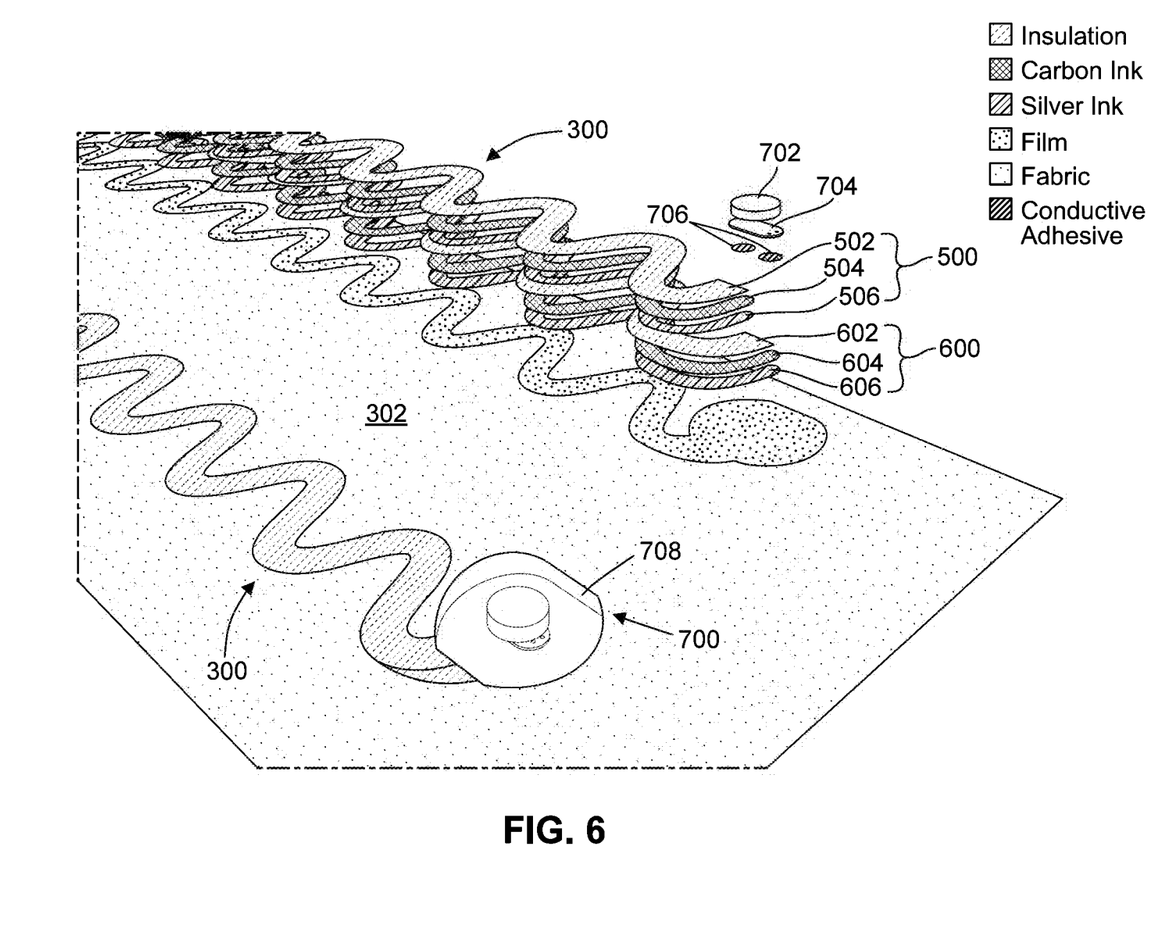
FIG. 6 is a partial exploded view of a capacitive sensor system according to embodiments of the present invention.

Turning to FIG. 6, to illustrate additional features along with general layering structure of capacitive sensor systems 100, 200, and 300, FIG. 6 shows a partial exploded view of an exemplary layering structure (similar to FIG. 5) according to an embodiment of various capacitive sensor systems as disclosed herein. As shown, capacitive sensor systems 100, 200, and 300 may include at least two conductor assemblies, for example, conductor assembly 500 and conductor assembly 600, disposed below conductor assembly 500. FIG. 6 additionally shows exemplary feedback module 700. In some embodiments, feedback module 700 includes, for example, haptic motor 702, which may provide haptic feedback to an individual. In some embodiments, a haptic circuit 704, e.g., a printed circuit board, may be operatively coupled to haptic motor 702, as well as the capacitive sensor system. This coupling occurs through connections 706, for example. Connections 706 include, for example, conductive adhesive. In some embodiments, other connection types may be used, for example, soldering, mechanical connectors, and the like. In some embodiments, feedback module 700 includes a housing 708. In some embodiments, housing 708 may be an elastomer overmolded assembly, encasing the feedback module 700. In some embodiments, housing 708 may be other materials, for example, a plastic, metal, or fabric material.

Figure 7:
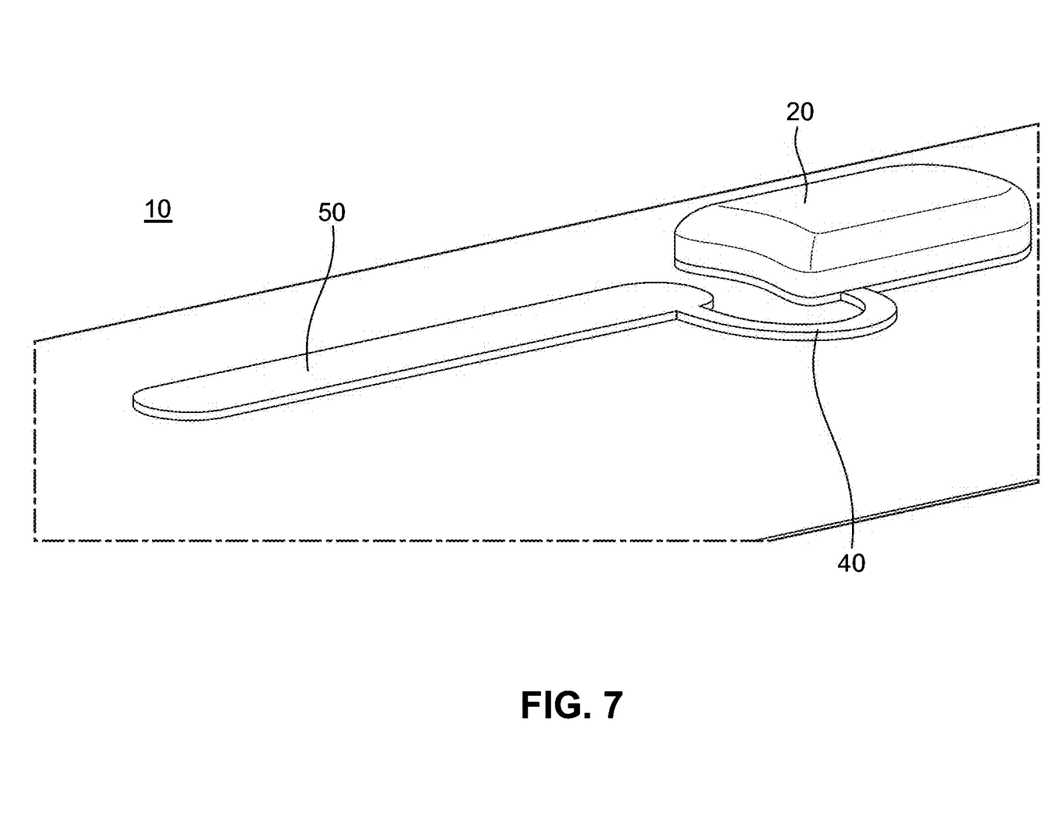
FIG. 7 is an illustration of a capacitive sensor system with an electronic module according to embodiments of the present invention.
Figure 8:
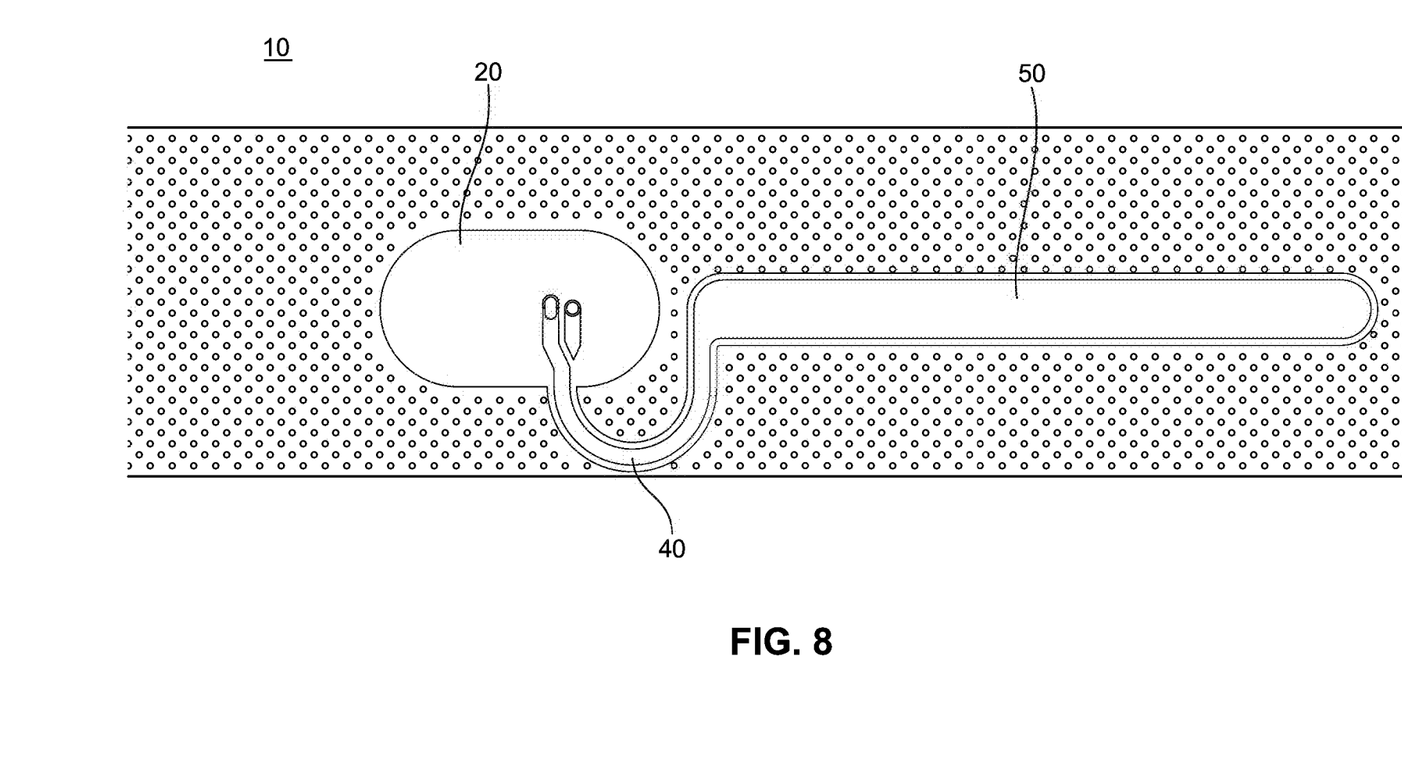
FIG. 8 illustration of a capacitive sensor system with an electronic module according to embodiments of the present invention.

Turning to FIG. 7, a sensor system 10 is shown, which in some embodiments includes a stretchable sensor 50 (e.g., a stretchable capacitive sensor as disclosed above), an electronics module 20 in a housing coupled to the sensor 50, and a strain relief member 40 extending from the stretchable sensor and coupling to the electronics module. In some embodiments, module 20 may be encapsulated in a substrate, or in a film layer such as the film layer described above. In this regard, module 20 may be configured to be used without ports or jacks on the outer surface of the module. When integrated with a garment, for example, module 20 may be wholly encapsulated in a fabric, such that it is hidden from view. In some embodiments, strain relief member 40 extends off axis to the stretching direction of sensor 50. In this regard, strain relief member 40 may be configured such that sensor 50 does not respond to movement of the strain relief member 40. As shown, the connections to the strain relief member 40 and the electronics module 20 (or connections to the strain relief member 40 and sensor 50) are positioned such that the trace is allowed to bend/buckle out of plane relative to the general plane of the electronics module 20 or sensor 50, thereby increasing strain relief. In some embodiments, this avoids formation of fissures or cracks due to material fatigue from either strain cycling or large stress magnitudes. Turning to FIG. 8, an top view embodiment of sensor system 10 is shown similar to FIG. 7, which in some embodiments includes a stretchable sensor 50 (e.g., a stretchable capacitive sensor as disclosed above), an electronics module 20 in a housing coupled to the sensor 50, and a strain relief member 40 extending from the stretchable sensor and coupling to the electronics module. In some embodiments, as shown in FIG. 8, strain relief member 40 may extend substantially perpendicularly to a longitudinal direction from stretchable sensor 50 (e.g., direction the sensor is designed to stretch and thus measure strain) at the location it couples to the electronics module. In some embodiments, the film layers (as described above) may include a cutout pattern, such that the coupling connection from the sensor 50, strain relief member 40, and electronics module 20 are flush with each other, such that the sensor components lay flat. In this regard, conductive adhesive portions (used in connections 706, for example) may be applied with even pressure.

Advantageously, as opposed to smart phone or smart watch systems, integrated garment sensor systems such as the sensor 50 coupled with module 20 may give individuals freedom to be mindful of their performance without additional distractions. Advantageously, data may be captured and uploaded and reviewed later, after an activity, which may aid in the individual staying mindful throughout their activity. Also, when coupled with a haptic module, gentle haptic feedback may be given to the individual during the activity, without the need for viewing a screen, or listening for audio feedback, for example. Additionally, being able to focus generally on the activity at hand, rather than raising an arm or looking down, avoids introducing inefficient body positioning or form into the athletic activity. In some embodiments, sensor 10 may function as an actuator, or input device, sending signals to module 20 when particular contact is detected.

In some embodiments, system 10 is used to detect changes in an individual's direction of motion. System 10 according to the present invention can also be worn by individuals and used to detect and/or track other motions such as, for example, motions associated with push-ups, pull-ups, weightlifting, diving, gymnastics, et cetera.

By using the system 10 described above, embodiments of the present invention may advantageously enable the individual 1 (or their coach, teammate, a spectator, friends, competitors, etc.) to obtain this or other information about the motion of the individual's 1 body or the motion of a piece of the individual's 1 athletic equipment during or after the course of the athletic activity.

While various embodiments of the present invention are described in the general context of activity, the present invention is not so limited and may be applied in a variety of different sports or athletic activities including, for example, running, sports of soccer (i.e., football), basketball baseball, bowling, boxing, cricket, cycling, football (i.e., American football), golf, hockey, lacrosse, rowing, rugby, running, skateboarding, skiing, surfing, swimming, table tennis, tennis, or volleyball, or during training sessions related thereto.

Further, while in use, system 10 may not require any additional device, such as electronic devices such as smart phones or smart watches. However, in some embodiments, system 10 may include a number of different software modules capable of providing training support or other interaction to individuals 1, either while the individual is engaged in an activity or after the individual engages in an activity and is reviewing their performance. Each module may support one or more graphical user interfaces ("GUIs") capable of being presented to an individual 1 using the system 10.

A GUI may offer, for example, graphical elements, visual indicators, and/or text to represent information and actions available to the individual 1. The individual 1 may use a physical input device, such as keyboard or scroll ball to interact with the GUI of the system 10, for example, on an electronic device. Alternatively, the individual 1 may use a touch screen to interact directly with what is displayed. Various touch screens such as, for example, resistive or capacitive touch screens, may be employed.

Those skilled in the art will appreciate that alternative or additional software modules and sub-modules may be implemented in order to provide or extend the described or additional functionalities to the individual 1 using an electronic device. For example, the software configuration of software stored on an electronic device may include a device operating system, which may be one of the commercially available mobile phone operating systems such as, for example, BlackBerry OS, iPhone OS, Windows Mobile, Symbian, LINUX, WebOS, or Android. The device operating system may also have an associated application programming interface through which middleware and application programs may access the services of the operating system.

Various aspects of the present invention, or any parts or functions thereof, may be implemented using hardware, software, firmware, tangible non-transitory computer readable or computer usable storage media having instructions stored thereon, or a combination thereof and may be implemented in one or more computer systems or other processing systems.

As discussed, program products, methods, and systems for providing robotic training services of the present invention can include any software application executed by one or more electronic devices. An electronic device can be any type of computing device having one or more processors. For example, the electronic device can be a workstation, mobile device (e.g., a mobile phone, personal digital assistant, tablet computer, or laptop), computer, server, compute cluster, server farm, game console, set-top box, kiosk, embedded system, a gym machine, a retail system or retail enhancement system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Software platform may include or accept computer programs (also called computer control logic, programming data, etc.), which may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In some embodiments, the one or more processors can be part of a computing device incorporated in a clustered computing environment or server farm. Further, in some embodiments, the computing process performed by the clustered computing environment may be carried out across multiple processors located at the same or different locations.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

It is to be understood that the phraseology or terminology used herein is for the purpose of description and not of limitation. The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

Further details of the noted systems and methods are set forth in co-pending U.S. application Ser. No. 15/862,299, filed concurrently herewith, which is incorporated by reference herein in its entirety for all purposes.

What is claimed is:

1. A capacitive sensor, comprising,
a stretchable substrate;
a first conductor assembly disposed in a serpentine pattern on a first side of the substrate and having first and second terminal ends coupled to the first side of the substrate; and
a second conductor assembly positioned above the first conductor on the first side of the substrate and having first and second terminal ends coupled to the first side of the substrate,
wherein one of the first and second terminal ends of the first conductor assembly is offset from a corresponding one of the first and second terminal ends of the second conductor assembly,
wherein the second conductor assembly, other than at the first and second terminal ends, is disposed above and follows the serpentine pattern of the first conductor assembly in an overlapping manner between the first and second terminal ends, and
wherein the first and second conductor assemblies are configured to measure a capacitance based upon a change in a capacitive area defined by the first and second conductor assemblies.

2. The capacitive sensor of claim 1, wherein the first terminal end of each of the first and second conductor assemblies extend substantially parallel to one another.

3. The capacitive sensor of claim 1, wherein the first terminal end of each of the first and second conductor assemblies is offset from one another.

4. The capacitive sensor of claim 1, further comprising a circuit operatively coupled to the first terminal end of each of the first and second conductor assemblies.

5. The capacitive sensor of claim 4, further comprising a haptic motor operatively coupled to the circuit that is configured to provide haptic feedback to an individual.

6. The capacitive sensor of claim 1, wherein the serpentine pattern of the first and second conductor assemblies have a constant pitch between adjacent peaks of the serpentine pattern.

7. The capacitive sensor of claim 1, wherein the first conductor assembly comprises a first layer and a second layer disposed above the first layer.

8. The capacitive sensor of claim 7, wherein the first layer is a silver ink layer and the second layer is a carbon ink layer.

9. The capacitive sensor of claim 8, wherein the first conductor assembly further comprises an insulation layer disposed above the second layer.

10. The capacitive sensor for claim 1, wherein the substrate comprises a stretchable base layer configured to provide a smooth surface for the first conductor assembly.

11. The capacitive sensor of claim 10, wherein the base layer is a polyurethane film.

12. A capacitive sensor, comprising, a stretchable substrate;

a first conductor assembly disposed in a serpentine pattern on the substrate and having a first terminal end coupled to a first side of the substrate; and a second conductor assembly having a second terminal end coupled to the first side of the substrate, wherein the first terminal end and the second terminal end are offset from one another along the first side of the substrate, wherein the second conductor assembly overlaps the first conductor on the first side of the substrate and follows the serpentine pattern of the first conductor assembly, and wherein the first and second conductor assemblies are configured to measure a capacitance based upon a change in a capacitive area defined by the first and second conductor assemblies.

* * * * *

UNITED STATES PATENT AND TRADEMARK OFFICE
CERTIFICATE OF CORRECTION

PATENT NO. : 11,852,509 B2
APPLICATION NO. : 17/327175
DATED : December 26, 2023
INVENTOR(S) : Bryce Beamer Page 1 of 1

It is certified that error appears in the above-identified patent and that said Letters Patent is hereby corrected as shown below:

On the Title Page

Item (54), and in the Specification, Column 1, Lines 1-2, change title from "CAPACITIVE SENSOR SYSTEMS AND METHOD" to --CAPACITIVE SENSOR SYSTEMS AND METHODS--.

In the Claims

In Column 13, Line 21, Claim 10, change "The capacitive sensor for" to --The capacitive sensor of--.

Signed and Sealed this
Ninth Day of April, 2024

Katherine Kelly Vidal

Katherine Kelly Vidal
*Director of the United States Patent and Trademark Office*